United States Patent [19]

Ohashi et al.

[11] Patent Number: 4,499,076

[45] Date of Patent: Feb. 12, 1985

[54] ELEMENTAL DIETS FOR LIVER DISEASES

[75] Inventors: Hiroyuki Ohashi, Kawasaki; Ikuo Ohara, Yokohama; Toru Takami, Yokosuka, all of Japan

[73] Assignee: Ajinomoto Company Incorporated, Tokyo, Japan

[21] Appl. No.: 453,832

[22] Filed: Dec. 28, 1982

[30] Foreign Application Priority Data

Jan. 22, 1982 [JP] Japan .................................. 57-8599

[51] Int. Cl.$^3$ ..................... A61K 31/07; A61K 31/12; A61K 31/23; A61K 31/40; A61K 31/44; A61K 31/59; A61K 31/68; A61K 31/70; A61K 31/195; A61K 31/355; A61K 31/365; A61K 31/415; A61K 31/455; A61K 31/685; A61K 33/06; A61K 33/14; A61K 33/26; A61K 33/34; A61N 43/78

[52] U.S. Cl. ..................... 424/143; 424/145; 424/147; 424/153; 424/154; 514/54; 514/58

[58] Field of Search .................. 424/319, 274, 273

[56] References Cited

U.S. PATENT DOCUMENTS

| | | | |
|---|---|---|---|
| 3,697,287 | 10/1972 | Winitz et al. | 424/319 |
| 3,698,912 | 10/1972 | Winitz et al. | 424/319 |
| 3,773,930 | 11/1973 | Mohammed | 424/319 |
| 3,920,838 | 11/1975 | Flatt et al. | 424/319 |
| 3,950,529 | 4/1976 | Fischer et al. | 424/273 |

*Primary Examiner*—Stanley J. Friedman
*Attorney, Agent, or Firm*—Oblon, Fisher, Spivak, McClelland & Maier

[57] ABSTRACT

An elemental diet of amino acids, carbohydrates, fats, vitamins and minerals.

9 Claims, No Drawings

ELEMENTAL DIETS FOR LIVER DISEASES

This invention relates to new elemental diets for liver diseases.

The basic therapy for liver diseases is a diet therapy. It has heretofore been thought that the diet therapy for liver diseases is to prevent the catabolism with high energy, high protein and promote the regeneration of liver cells for the purpose of recovering the hepatic function. However, depending on the severity of the hepatic disorder, unless the amount of protein to be ingested is restricted, substances which would cause hepatic encephalopathy such as ammonia, amines, short-chain fatty acids etc. accumulate as the result of the decrease in the metabolic function of the liver, and hence the disease is aggravated. Therefore, for patients with whom oral ingestion is possible, a low protein diet is administered. However, since it is difficult to seek to inhibit the catabolism of the somatic protein if the therapy is intended for a long period of time, medium level protein has been ingested in combination with lactulose, antibiotics etc., but side effects, such as diarrhoea, microbisme slectionné et substitué, even renal insufficiency, etc., are too grave to be neglected, and thus an adequate effect cannot be expected. Further, in the case of more serious patients with whom oral ingestion is not possible, only a passive therapy which seeks to improve encephalopathy and protect the liver by intravenous administration of glucose is merely practiced.

An elemental diet which contains amino acids, carbohydrates, fats, vitamins, minerals etc. has been proposed for patients with whom oral ingestion was not possible (Stephens, R. V., et al, Ann. Surg., 170 642 (1969)), but this is hardly said suitable for the conditions of liver diseases. Furthermore, even by intravenous hyperalimentation, as long as a conventional amino acid composition is employed, appropriate nutritional management cannot be achieved.

In recent years, researches on the pathophysiology of various diseases, especially on the blood amino acid patterns, have been increasingly carried out, and accordingly, also in the case of liver diseases, the alterations in plasma amino acids have been made clear. For example, the concentrations of branched-chain amino acids such as valine, leucine, isoleucine are lowered than the normal level, whereas aromatic amino acids such as phenylalanine, tyrosine, tryptophan and sulfur-containing amino acids such as methionine, taurine etc. are increased.

Such abnormality in the plasma amino acid level is believed due to the decrease of the metabolic function of the liver. Recently, there was proposed an approach for treating encephalopathy by rectifying the abnormality of the plasma amino acid level in hepatic insufficiency by intravenous administration of an amino acid solution (see Fischer, J. E., et al., Surgery, 80 77-91 (1976)).

The present inventors have been intensively studying with the view of developing an elemental diet for the purpose of nutritional management of patients with serious liver disease, and have finally accomplished this invention.

Accordingly, this invention is an elemental diet which comprises amino acids, carbohydrates, fats, vitamins and minerals, which elemental diet is characterized by containing at least isoleucine, leucine, valine, phenylalanine, tyrosine, tryptophan, threonine, glycine, serine and arginine, so that (a) the molar ratio of (isoleucine+leucine+valine+arginine)/(phenylalanine+tyrosine+tryptophan)=50–60;

(b) the molar ratio of (isoleucine+leucine+valine+arginine)/(glycine+serine+threonine)=4–5; and (c) the molar ratio of arginine/(glycine+serine+threonine)=0.8–1.0.

Preferably, it is an elemental diet which contains at least essential amino acids together with alanine, arginine, glycine, histidine, proline and serine in such composition as shown below.

| Amino Acid | Mole % |
| --- | --- |
| Isoleucine | 13.25–16.19 |
| Leucine | 16.25–19.87 |
| Valine | 13.86–16.94 |
| Lysine | 5.36–6.55 |
| Methionine | 0.79–0.97 |
| Phenylalanine | 0.71–0.87 |
| Threonine | 3.68–4.50 |
| Tryptophan | 0.27–0.33 |
| Alanine | 11.04–13.50 |
| Arginine | 10.02–12.24 |
| Glycine | 5.76–7.04 |
| Histidine | 1.99–2.43 |
| Proline | 4.56–5.58 |
| Serine | 2.46–3.00 |
| Total | 100 |

Further, if necessary, additives such as fungicides, emulsifiers etc. may also be incorporated.

The amino acids used in this invention may also include derivatives and adducts which may be assimilated as amino acids in vivo, and may also be used as salts of mineral acids such as hydrochloric acid, salts of organic acids such as acetic acid, malic acid etc., peptides, N-acylates, hydrates etc. In such a case, each amino acids may be incorporated in an amount to satisfy the above composition as calculated as the free from of the amino acid.

For example, such amino acids as lysine, histidine, arginine etc. may also be employed as salts such as the hydrochloride, acetate etc.

The amino acid content in the composition is 10–20% by weight or so.

The carbohydrates used in this invention are, for example, dextrin. Monosaccharides, oligosaccharides etc. may also be employed. The amount to be used as expressed in % by weight is generally 70–80% or so.

The fats used in this invention are, for example, soybean oil, corn oil, cotton seed oil etc. The amount to be used as expressed in % by weight is 2–4% or so, and by retaining such a low fat content, the solubility or emulsifiability may be enhanced and also diarrhoea due to fat degradation etc. may be minimized.

The vitamins used in this invention are, for example, Vitamin A such as retinol acetate, Vitamin $B_1$ such as thiamine hydrochloride, Vitamin $B_2$ such as riboflavin phosphate sodium, Vitamin $B_6$ such as pyridoxin hydrochloride, Vitamin $B_{12}$ such as cyanocobalamine, Vitamin C such as ascorbic acid, Vitamin $D_2$ such as ergocalciferol, Vitamin E such as tocopherol acetate, Vitamin $K_1$ such as phytonadione, calcium pantothenate, nicotinic acid amine, biotin, folic acid, chlorine bitartrate etc.

The amount of the total vitamins used is 100-200 mg or so pr 100 g of the nutrient composition.

The minerals used in this invention are, for example, iron such as iron gluconate dihydrate, copper such as copper sulfate pentahydrate, manganese such as manganese sulfate pentahydrate, zinc such as zinc sulfate heptahydrate, potassium such as potassium gluconate, potassium chloride etc., iodine such as potassium iodine, sodium such as sodium citrate dihydrate, calcium such as calcium glycerophosphate, magnesium such as magnesium sulfate heptahydrate, etc.

The amount of the total minerals used is 4,000-7,000 mg or so per 100 g of the nutrient composition.

Since in the liver diseases, especially in liver cirrhosis, the reduction in exchangeable potassium (Ke) is observed, the amount of potassium used may be greater as compared with in the conventional nutrient or elemental diet. Desirably, about 1,500-2,500 mg of potassium gluconate or about 500-1,000 mg of potassium chloride is employed per 100 g of the nutrient composition.

Since the zinc is expected to have an effect to protect the liver cell membrane, this is better used in an amount greater than the conventional level. Therefore, 15-25 mg of zinc sulfate heptahydrate is suitable per 100 g of the nutrient composition.

When the composition of this invention is used as a product, by employing a fungicide such as potassium sorbate, and an emulsifier such as polysorbate, soybean phospholipid etc. as additives, proliferation of bacteria in powder or solution may be inhibited, and further, since it is easily dissolved or emulsified, its administration using a tube or its oral administration may be conducted very smoothly.

Where the nutrient produced by employing this invention is to be administered to a patient with liver disease, it is more easily administered when it is emulsified and homogenized, and this is also preferred from an aspect of digestion and absorption.

The product of this invention may be administered either intraintestinally or orally.

Where administered intraintestinally using a tube, it is advised to use it as a solution of e.g. about 5-40 w/v % using water or lukewarm water.

The products of this invention may be widely applied as nutrients for liver diseases for the purpose of improving the poor hepatic functioning conditions, for instance, for nutrition management before and after operations on patients with liver cirrhosis, patients with hepatoma, patients with chronic hepatitis etc., and/or for prophylaxis and awakening of hepatic coma in the case of hepatic insufficiency, and for promotion of the liver regeneration in the case of the liver excision.

This invention is more particularly described by the following examples.

EXAMPLE 1

Materials set forth in Table 1 were uniformly dry mixed.

TABLE 1

Composition of Elemental Diet for Liver Disease (per 100 g)

| | | | | | |
|---|---|---|---|---|---|
| dextrin | 74.32 g | choline bitartrate | 105.0 mg | L-methionine | 0.146 g |
| Soybean oil | 3.50 g | iron gluconate dihydrate | 11.52 mg | L-phenylalanine | 0.146 g |
| phytonadione | 55.0 μg | copper sulfate pentahydrate | 1.02 mg | L-threonine | 0.545 g |
| retinol acetate | 0.310 mg | manganese fulfate pentahydrate | 1.59 mg | L-tryptophan | 0.070 g |
| thiamine hydrochloride | 1.121 mg | zinc sulfate heptahydrate | 19.70 mg | L-alanine | 1.222 g |
| riboflavin phosphate sodium | 1.209 mg | magnesium sulfate heptahydrate | 507.0 mg | L-arginine | 2.170 g |
| pyridoxin hydrochloride | 0.839 mg | Potassium iodine | 40.8 μg | glycine | 0.538 g |
| cyanocobalamine | 2.70 μg | potassium chloride | 991.5 mg | L-histidine | 0.383 g |
| ascorbic acid | 29.25 mg | potassium gluconate | 2.110 g | L-proline | 0.652 g |
| ergocarliciferol | 4.78 μg | calcium glycerophosphate | 1.602 g | L-serine | 0.321 g |
| tocopherol acetate | 20.65 mg | sodium citrate dihydrate | 980.8 mg | soybean phospholipid | 170 mg |
| calcium pantothenate | 2.06 mg | L-isoleucine | 2.162 g | polysorbate 80 | 50 mg |
| nicotinic acid amide | 4.13 mg | L-leucine | 2.652 g | potassium sorbate | 150 mg |
| biotin | 49.0 μg | L-Valine | 2.019 g | L-ascorbyl steariate | 2 mg |
| folic acid | 0.165 mg | L-lysine acetate | 1.374 g | anhydrous citric acid | 1015 mg |

When employed orally, the above-described mixture is either formed into a paste using water or dissolved in a suitable amount of water. At this time, natural and/or synthetic food flavors such as chocolate, peppermint, custard, pistachio etc. may also be mixed and incorporated.

When employed intraintestinally, a standard solution for administration may be obtained by dissolving 80 g of the above-described mixture in lukewarm water and making the total volume 300 ml (26.7% (w/v)). Further, depending on the necessity, solutions of varied concentrations of 5-30% (w/v) are prepared and put into bags for administering preparations, and each soflution may be administered to the duodenum or the jejunum of a patient via a catheter.

The results of the experiments on the effectiveness of the preparations according to this invention as nutrients for liver diseases using animal models are now explained.

EXAMPLE 2

Awakening Effect on Ammonia-induced Coma

The preparation prepared in Example 1 was employed as a 25% (w/v) solution (Test Group 1). The comparison control was that employing a commercial elemental diet ("Elental" trademark of Ajinomoto Co., Inc.) (Test Group 2). The other one was that in which the amino acid portion in Group 2 was replaced by a composition "FO-80" (See Japanese Patent Application Laid-open No.118839/1976) (Test Group 3). The test animals used were SD strain male rats weighing about 240 g. After fasting overnight, the liver was excised (by 70%), and a gastric fistula tube was provided as an administration route for the elemental diet. Each solution was continuously infused at a rate of 7.3 ml/kg/hr up to 24 hours after the liver excision, and at 10.4 ml/kg/hr thereafter. About 48 hours after the liver excision, 2.6 ml/kg of a 10% (w/v) ammonium chloride was intraperitoneally administered, and the coma conditions were checked by the presence of righting reflex. The results are shown in Tables 2 and 3.

TABLE 2

| | n | mortality (%) | comatose time (min) |
|---|---|---|---|
| Test Group 1 | 6 | 0 | 38 ± 9$^a$ |
| Test Group 2 | 5 | 40 | 77 ± 16$^b$ |
| Test Group 3 | 6 | 33 | 58 ± 24$^b$ |

$^{a, b}$: Means within the same column and followed by the same superscript letter are not significantly different. (P < 0.05, , x̄± SD)

TABLE 3

| | n | BCAA/AAA | BCAA/(AAA + Tau + Met) | (BCAA + Arg)/(Thr + Ser + Gly) |
|---|---|---|---|---|
| Normal control | 5 | 2.87 ± 0.35$^{ab}$ | 0.60 ± 0.05$^b$ | 0.85 ± 0.11$^b$ |
| Test Group 1 | 6 | 3.92 ± 1.64$^a$ | 0.97 ± 0.29$^a$ | 1.06 ± 0.18$^b$ |
| Test Group 2 | 3 | 1.57 ± 0.30$^{ab}$ | 0.44 ± 0.06$^b$ | 0.40 ± 0.07$^a$ |
| Test Group 3 | 4 | 1.94 ± 0.90$^b$ | 0.62 ± 0.18$^b$ | 0.52 ± 0.16$^a$ |

BCAA: branched-chain amino acid (sum of Leu, Ile and Val)
AAA: aromatic amino acid (sum of Phe, Tyr and Trp)
a,b,c,: P < 0.05

The results were, as shown in Table 2, such that Test Group 1 exceeded Test Group 2 and 3 in the death rate and the coma period. Furthermore, as shown in Table 3, the molar ratio of the plasma free amino acid levels immediately after awakening from coma, especially the ratio of the branched-chain amino acids to the aromatic amino acids, moreover the ratio to that to which methionine and taurine were added, etc. were in co-relation with the results of Table 2.

EXAMPLE 3

Effect to Promote Liver Regeneration

The test solutions same as in Example 2 were employed and Example 2 was repeated.

As the test animals, SD strain male rats (weighing about 240 g) were employed. After the liver excision, each test solution was administered as in Example 2, and 5 days after the liver excision, the liver regeneration ratio was measured and the results are shown in Table 4.

TABLE 4

| | n | Liver Regeneration Ratio % |
|---|---|---|
| Test Group 1 | 9 | 89.4 ± 23.7$^a$ |
| Test Group 2 | 4 | 53.1 ± 20.7$^b$ |
| Test Group 3 | 5 | 63.4 ± 9.1$^b$ |

$$\text{Liver Regeneration Ratio} = \frac{\text{Regenerating Liver (at autopsy)} - \text{Residual Liver (estimated at excising)}}{\text{Excised Liver}} \times 100$$

a,b: P < 0.05

From Table 4, it can be understood that the liver regeneration is promoted in the order of Group 1 > Group 3 > Group 2.

EXAMPLE 4

Nutritional Effect on Rats with Chronic Hepatic Disorder

The test solutions same as in Example 2 were employed. The test animals used were SD strain male rats weighing about 170 g. A 60% (v/v) solution of carbon tetrachloride in olive oil was administered at 1 ml/kg twice a week for 10 weeks, to prepare experimental hepatic fibrosis, and further rats from which about 70% of the liver had been removed were used as models with chronic hepatic disorder. The administration of the test solution was conducted similarly as in Example 2, and continued for 7 days. The results are shown in Table 5.

TABLE 5

| | n | survival ratio % | nitrogen balance mgN/3 days | hepaplastin test % |
|---|---|---|---|---|
| Normal control | 5 | — | — | 70.8 ± 8.4$^a$ |
| Test Group 1 | 7 | 100 | −34.2 ± 83.5 | 72.0 ± 6.5$^a$ |
| Test Group 2 | 7 | 57 | −122.6 ± 121.5 | 50.0 ± 13.1$^b$ |
| Test Group 3 | 7 | 100 | −87.8 ± 102.7 | 68.0 ± 15.1$^a$ |

$^{a, b}$: P < 0.05

As evident from Table 5, there were death cases in Group 2, whereas the other groups recovered successfully. The nitrogen balance was good in Group 1. In the hepaplastin test which indicated the synthetizing activity of blood coagulation proteins, the recovery was in the order of Group 1 > Group 3 > Group 2. Further, Group 1 showed a better effect to improve the molar ratio of the plasma amino acid level as compared with the other groups (see Table 6).

TABLE 6

| | n | BCAA/AAA | BCAA/(AAA + Tau + Met) | (BCAA + Arg)/(Thr + Ser + Gly) |
|---|---|---|---|---|
| Normal control | 4 | 2.38 ± 0.05$^a$ | 0.81 ± 0.03$^a$ | 0.70 ± 0.07 |
| Test Group 1 | 5 | 1.99 ± 0.14$^b$ | 0.63 ± 0.05$^b$ | 0.67 ± 0.18 |

TABLE 6-continued

|  | n | BCAA/AAA | BCAA/(AAA + Tau + Met) | (BCAA + Arg)/(Thr + Ser + Gly) |
|---|---|---|---|---|
| Test Group 2 | 4 | $1.56 \pm 0.10^d$ | $0.50 \pm 0.07^c$ | $0.56 \pm 0.07$ |
| Test Group 3 | 6 | $1.76 \pm 0.10^c$ | $0.59 \pm 0.06^c$ | $0.56 \pm 0.06$ |

Abbreviations are same in Table 3.
a,b,c,d: $P < 0.05$

What is claimed is:

1. An elemental diet which comprises essential amino acids, carbohydrates, fats, vitamins and minerals together with alanine, arginine, glycine, histidine, proline and serine in such composition as shown below:

| Amino Acid | Mole % |
|---|---|
| Isoleucine | 13.25–16.19 |
| Leucine | 16.25–19.87 |
| Valine | 13.86–16.94 |
| Lysine | 5.36–6.55 |
| Methionine | 0.79–0.97 |
| Phenylalanine | 0.71–0.87 |
| Threonine | 3.68–4.50 |
| Tryptophan | 0.27–0.33 |
| Alanine | 11.04–13.50 |
| Arginine | 10.02–12.24 |
| Glycine | 5.76–7.04 |
| Histidine | 1.99–2.43 |
| Proline | 4.56–5.58 |
| Serine | 2.46–3.00 |
| Total | 100 |

2. The elemental diet of claim 1 further comprising an amino acid content of from about 10% to 20% by weight.

3. The elemental diet of claim 1 further comprising dextrin.

4. The elemental diet of claim 1 further comprising monosaccharides or oligosaccharides in an amount of about 70% to 80% by weight.

5. The elemental diet of claim 1 further comprising soybean oil, corn oil, or cotton seed oil in an amount of about 2% to 4% by weight.

6. The elemental diet of claim 1 further comprising Vitamin A, Vitamin $B_1$, Vitamin $B_6$, Vitamin $B_{12}$, Vitamin C, Vitamin $D_2$, Vitamin E, Vitamin $K_1$, calcium pantothenate, nicotinic acid amide, biotin, folic acid, or choline bitartrate in a total amount of from 100 mg to 200 mg per 100 g of said elemental diet.

7. The elemental diet of claim 1 further comprising iron gluconate dihydrate, copper sulfate pentahydrate, zinc sulfate heptahydrate, potassium gluconate, potassium chloride, potassium iodine, sodium citrate dihydrate, calcium glycerophosphate, or magnesium sulfate heptahydrate in a total amount of from about 4,000 mg to 7,000 mg per 100 g of said elemental diet.

8. The elemental diet of claim 7 further comprising from about 1,500 mg to 2,500 mg of potassium gluconate per 100 g of said elemental diet.

9. The elemental diet of claim 7 further comprising from about 500 mg to 1,000 mg of potassium chloride per 100 g of said elemental diet.

* * * * *

UNITED STATES PATENT AND TRADEMARK OFFICE
CERTIFICATE OF CORRECTION

PATENT NO.  : 4,499,076
DATED       : February 12, 1985
INVENTOR(S) : Hiroyuki Ohashi et al It is certified that error appears in the above-identified patent and that said Letters Patent is hereby corrected as shown below:

Column 2, line 67, change "amine" to --amide--.

Column 3, line 2, change "pr" to --per--.

Column 4, line 63, change "soflu-" to --solu---

Column 6, Table 5, line 52, line should be underlined.

Signed and Sealed this

Third Day of December 1985

[SEAL]

Attest:

DONALD J. QUIGG

Attesting Officer

Commissioner of Patents and Trademarks